(12) United States Patent
Hayes

(10) Patent No.: US 6,261,275 B1
(45) Date of Patent: Jul. 17, 2001

(54) EYE AND WOUND WASHING DEVICE

(76) Inventor: Elberta Hayes, 62078 Bolar Rd., McArthur, OH (US) 45651

( * ) Notice: Subject to any disclaimer, the term of this patent is extended or adjusted under 35 U.S.C. 154(b) by 0 days.

(21) Appl. No.: 09/276,102

(22) Filed: Mar. 25, 1999

(51) Int. Cl.[7] .................................................. A61M 35/00
(52) U.S. Cl. ............................................... 604/294; 4/620
(58) Field of Search .................................. 604/294, 296, 604/297, 300–302; 4/619, 620, 623, 624, 615; 239/24, 25, 28, 29, 30, 543, 590.3, 332

(56) References Cited

U.S. PATENT DOCUMENTS

| | | | |
|---|---|---|---|
| 3,809,315 | * | 5/1974 | Wright ..................................... 239/31 |
| 4,627,845 | * | 12/1986 | DeMotte ............................... 604/295 |
| 4,675,924 | * | 6/1987 | Allison et al. ........................... 4/620 |
| 4,939,800 | * | 7/1990 | Fiorentino et al. ..................... 4/620 |
| 5,265,288 | * | 11/1993 | Allison ................................... 4/620 |
| 5,320,615 | * | 6/1994 | Van Keuren ........................ 604/297 |
| 5,530,972 | * | 7/1996 | Tanner ................................... 4/620 |
| 5,754,990 | * | 5/1998 | Gurries, II ............................. 4/620 |
| 5,836,927 | * | 11/1998 | Fried .................................... 604/300 |

* cited by examiner

*Primary Examiner*—Mark O. Polutta
*Assistant Examiner*—David J. Cho

(57) ABSTRACT

A new eye and wound washing device for irrigating eyes and wounds with fluids such as water or saline solutions. The inventive device includes a hollow tube member with at least one elongate arm tube portion extending from the proximal end of an elongate stem tube portion. The distal end of the stem tube portion has an opening into the hollow interior of the tube member and is connectable to a fluid reservoir to permit fluid flow from the fluid reservoir through the distal end opening into the hollow interior of the tube member. A first irrigator member is in fluid communication with the first arm tube portion and includes a plurality of irrigation apertures for permitting fluid flow therethrough from the interior of the tube member. The mounting portion of a first guide member is mounted to the first arm tube portion. The first guide member also includes an arcuate finger guide portion extending from the mounting portion.

10 Claims, 4 Drawing Sheets

EYE AND WOUND WASHING DEVICE

BACKGROUND OF THE INVENTION

1. Field of the Invention

The present invention relates to injury washing devices and more particularly pertains to a new eye and wound washing device for irrigating eyes and wounds with fluids such as water or saline solutions.

2. Description of the Prior Art

The use of injury washing devices is known in the prior art. More specifically, injury washing devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art injury washing devices include U.S. Pat. No. 5,320,615; U.S. Pat. No. 4,798,599; U.S. Pat. No. Des. 342,309; U.S. Pat. No. 4,939,800; U.S. Pat. No. 3,871,554; and U.S. Pat. No. 4,675,924.

While these devices fulfill their respective, particular objectives and requirements, the aforementioned patents do not disclose a new eye and wound washing device. The inventive device includes a hollow tube member with at least one elongate arm tube portion extending from the proximal end of an elongate stem tube portion. The distal end of the stem tube portion has an opening into the hollow interior of the tube member and is connectable to a fluid reservoir to permit fluid flow from the fluid reservoir through the distal end opening into the hollow interior of the tube member. A first irrigator member is in fluid communication with the first arm tube portion and includes a plurality of irrigation apertures for permitting fluid flow therethrough from the interior of the tube member. The mounting portion of a first guide member is mounted to the first arm tube portion. The first guide member also includes an arcuate finger guide portion extending from the mounting portion.

In these respects, the eye and wound washing device according to the present invention substantially departs from the conventional concepts and designs of the prior art, and in so doing provides an apparatus primarily developed for the purpose of irrigating eyes and wounds with fluids such as water or saline solutions.

SUMMARY OF THE INVENTION

In view of the foregoing disadvantages inherent in the known types of injury washing devices now present in the prior art, the present invention provides a new eye and wound washing device construction wherein the same can be utilized for irrigating eyes and wounds with fluids such as water or saline solutions.

The general purpose of the present invention, which will be described subsequently in greater detail, is to provide a new eye and wound washing device apparatus and method which has many of the advantages of the injury washing devices mentioned heretofore and many novel features that result in a new eye and wound washing device which is not anticipated, rendered obvious, suggested, or even implied by any of the prior art injury washing devices, either alone or in any combination thereof.

To attain this, the present invention generally comprises a hollow tube member with at least one elongate arm tube portion extending from the proximal end of an elongate stem tube portion. The distal end of the stem tube portion has an opening into the hollow interior of the tube member and is connectable to a fluid reservoir to permit fluid flow from the fluid reservoir through the distal end opening into the hollow interior of the tube member. A first irrigator member is in fluid communication with the first arm tube portion and includes a plurality of irrigation apertures for permitting fluid flow therethrough from the interior of the tube member. The mounting portion of a first guide member is mounted to the first arm tube portion. The first guide member also includes an arcuate finger guide portion extending from the mounting portion.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new eye and wound washing device apparatus and method which has many of the advantages of the injury washing devices mentioned heretofore and many novel features that result in a new eye and wound washing device which is not anticipated, rendered obvious, suggested, or even implied by any of the prior art injury washing devices, either alone or in any combination thereof.

It is another object of the present invention to provide a new eye and wound washing device which may be easily and efficiently manufactured and marketed.

It is a further object of the present invention to provide a new eye and wound washing device which is of a durable and reliable construction.

An even further object of the present invention is to provide a new eye and wound washing device which is susceptible of a low cost of manufacture with regard to both materials and labor, and which accordingly is then susceptible of low prices of sale to the consuming public, thereby making such eye and wound washing device economically available to the buying public.

Still yet another object of the present invention is to provide a new eye and wound washing device which provides in the apparatuses and methods of the prior art some of the advantages thereof, while simultaneously overcoming some of the disadvantages normally associated therewith.

Still another object of the present invention is to provide a new eye and wound washing device for irrigating eyes and wounds with fluids such as water or saline solutions.

Yet another object of the present invention is to provide a new eye and wound washing device which includes a hollow tube member with at least one elongate arm tube portion extending from the proximal end of an elongate stem tube portion. The distal end of the stem tube portion has an opening into the hollow interior of the tube member and is connectable to a fluid reservoir to permit fluid flow from the fluid reservoir through the distal end opening into the hollow interior of the tube member. A first irrigator member is in fluid communication with the first arm tube portion and includes a plurality of irrigation apertures for permitting fluid flow therethrough from the interior of the tube member. The mounting portion of a first guide member is mounted to the first arm tube portion. The first guide member also includes an arcuate finger guide portion extending from the mounting portion.

Still yet another object of the present invention is to provide a new eye and wound washing device that can be quickly directed at eyes or wounds to flush them with fluid.

Even still another object of the present invention is to provide a new eye and wound washing device that can deliver a wide variety of fluids such as water, saline solution, or an intravenous antibiotic solution.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
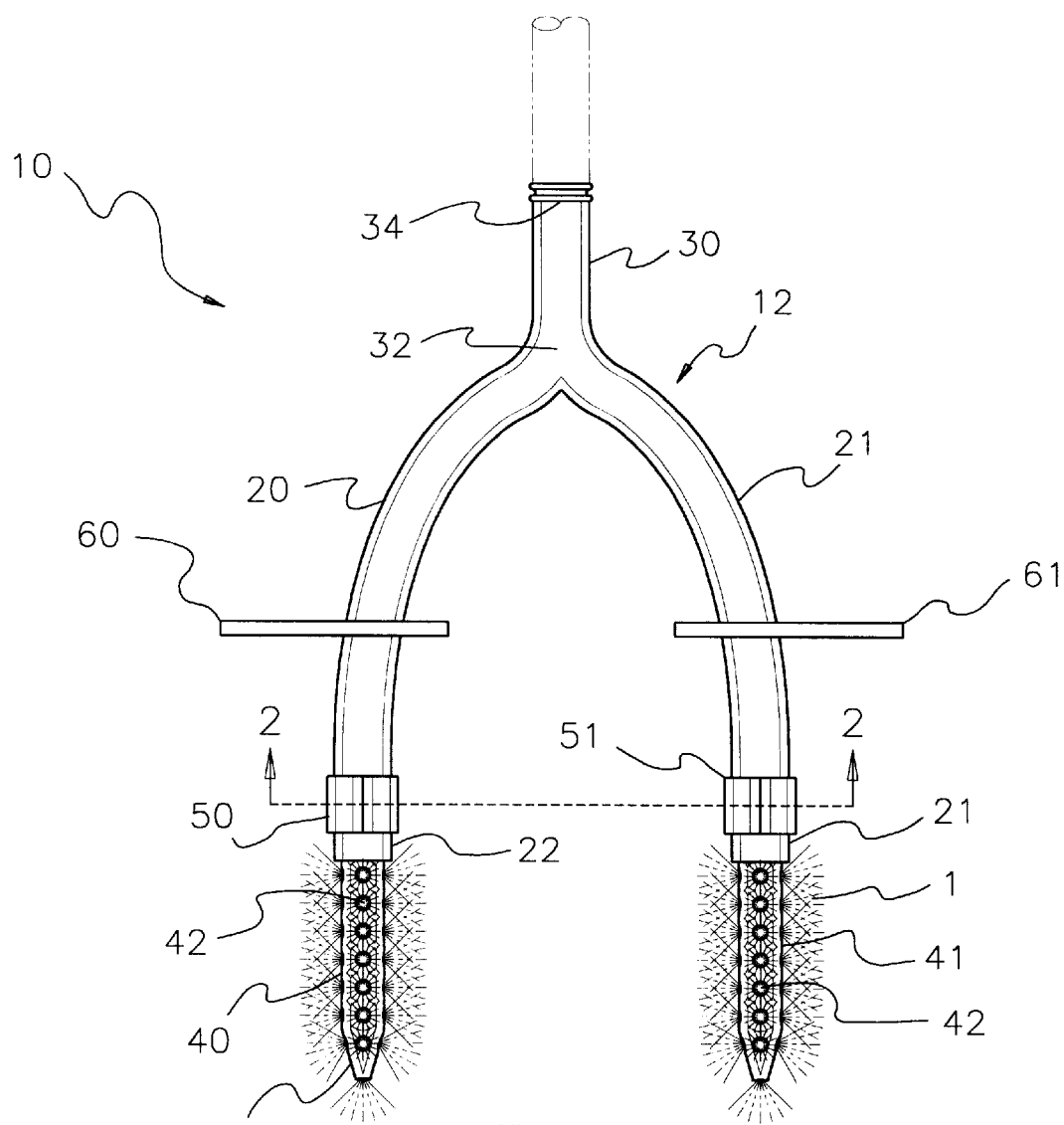
FIG. 1 is a side view of a new eye and wound washing device according to the present invention with fluid spraying from the irrigation members.

With reference now to the drawings, and in particular to FIGS. 1 through 5 thereof, a new eye and wound washing device embodying the principles and concepts of the present invention and generally designated by the reference numeral 10 will be described.

The eye and wound washing device 10 is designed for directing fluid 1, such as water or saline solution, to flush and irrigate an eye or a wound. As best illustrated in FIGS. 1 through 5, the eye and wound washing device 10 generally comprises a hollow tube member 12 with at least one elongate arm tube portion 20 extending from the proximal end 32 of an elongate stem tube portion 30. The distal end 34 of the stem tube portion 30 has an opening 36 into the hollow interior of the tube member 12 and is connectable to a fluid reservoir (not shown) to permit fluid flow from the fluid reservoir through the distal end opening 36 into the hollow interior of the tube member 12. A first irrigator member 40,41 is in fluid communication with the first arm tube portion 20 and includes a plurality of irrigation apertures 42 for permitting fluid flow therethrough from the interior of the tube member 12. The mounting portion 52 of a first guide member 50,51 is mounted to the first arm tube portion 20. The first guide member also includes an arcuate finger guide portion 54 extending from the mounting portion 52.

Preferably, tube member is Y-shaped having similar first and second elongate arm tube portions 20,21 and an elongate stem tube portion 30. The first and second arm tube portions 20,21 are both extended from the stem tube portion distal end 34. At the terminal end 22,23 of each of the arm tube portions 20,21 is an opening (not shown) into the hollow interior of the Y-shaped tube member 12.

Preferably, each the irrigation member 40,41 is coupled to their respective arm tube portion 20,21. Ideally, inserted into each arm tube portion terminal end 22,23 opening is the attachment end 44 of an irrigation member 40,41. Also ideally, the attachment ends 44 of the irrigation members 40,41 are detachable from their respective arm tube portion 20,21 to permit replacement and interchanging of irrigation members 40,41. Each irrigator member attachment end 44 has an opening (not shown) into the hollow interior of the irrigator member 40,41. The opening of the irrigation member attachment ends 44 are each in fluid communication with the terminal end opening of their respective arm tube portion 20,21 to permit fluid flow between the hollow interior of the Y-shaped tube member 12 and the hollow interiors of the irrigation members 40,41.

As shown in FIG. 1, each of the irrigation members 40,41 has a plurality of irrigation apertures 42. The irrigation apertures 42 provide an opening through the irrigation member 40,41 into the irrigation member 40,41 hollow interior to permit fluid flow from the interior of the irrigation member 40,41 to the outside to permit passing fluids 1 to spray or fountain so that fluid may be directed to irrigate and flush eyes or wounds.

Preferably, the terminus end 46 of each irrigation member 40,41 is tapered for aiding insertion of the irrigator member 40,41 into a wound so that the wound can be thoroughly irrigated with fluid.

Figure 2:
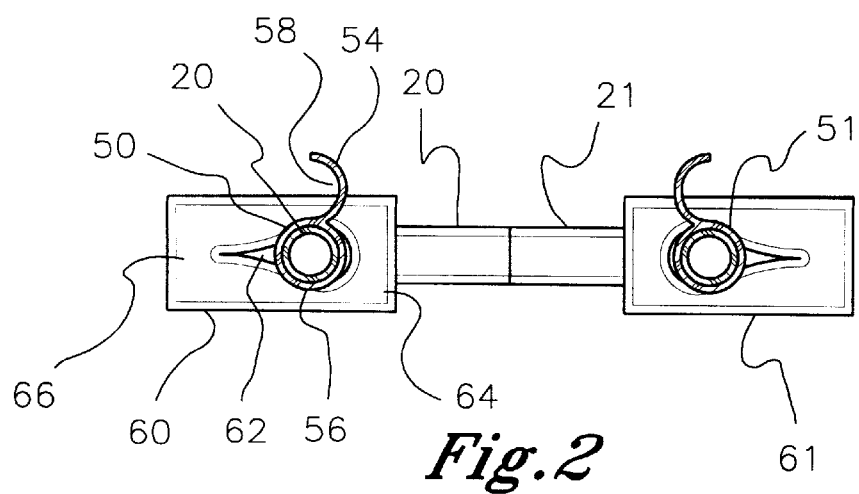
FIG. 2 is a cross sectional view of the present invention taken from line 2—2 of FIG. 2 detailing the closing tabs.

With particular reference to FIG. 2, a guide member 50,51 is mounted to each arm tube portion 20,21 of the tube member 12. Each guide member 50,51 has a mounting portion 52 with a mounting bore 56 through which the respective arm tube portion 20,21 is extended through.

Extending from each mounting portion 52 is the arcuate finger guide portion 54. The inner side of each finger guide portion 54 is curved to form a concavity 58 designed for receiving a finger to help guide positioning of the irrigation member toward an eye or a wound. Preferably, the outer sides of the finger guide portions 54 of the guide members 50,51 face each other so that the concavities 58 of the finger guide portions 54 open away from each other.

Figure 3:
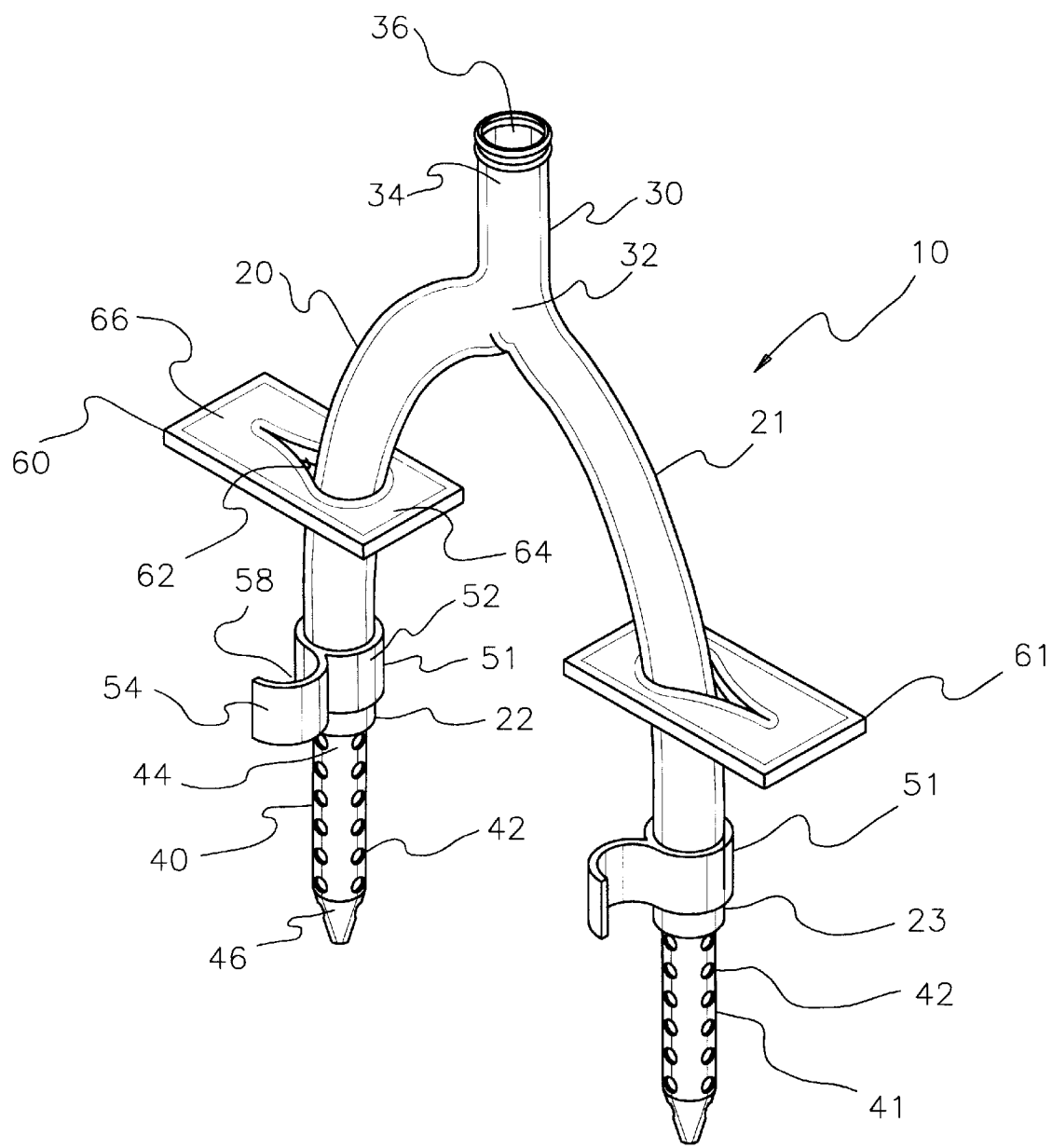
FIG. 3 is a perspective view of the present invention.
Figure 4:
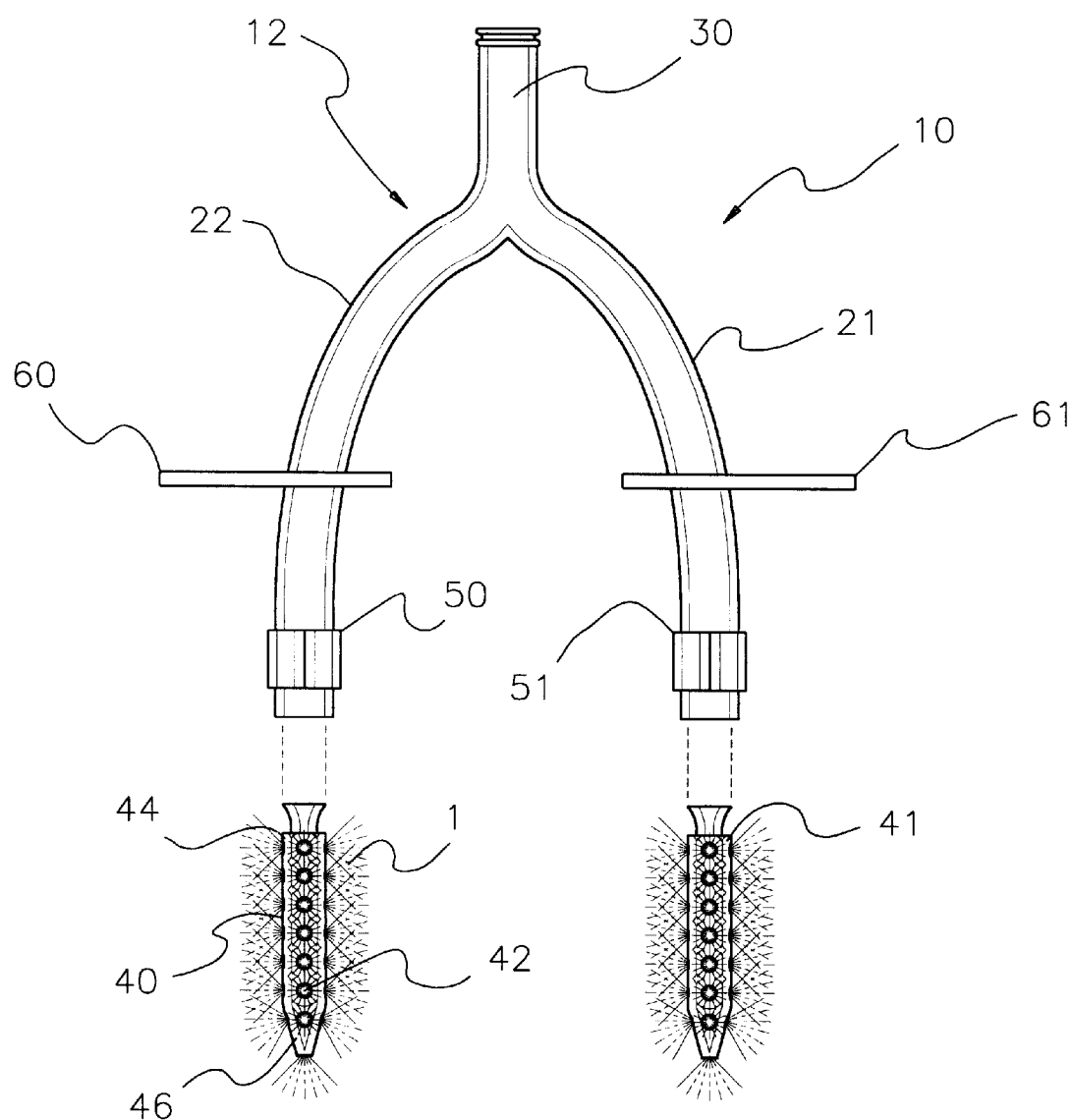
FIG. 4 is a exploded side view of the present invention.
Figure 5:
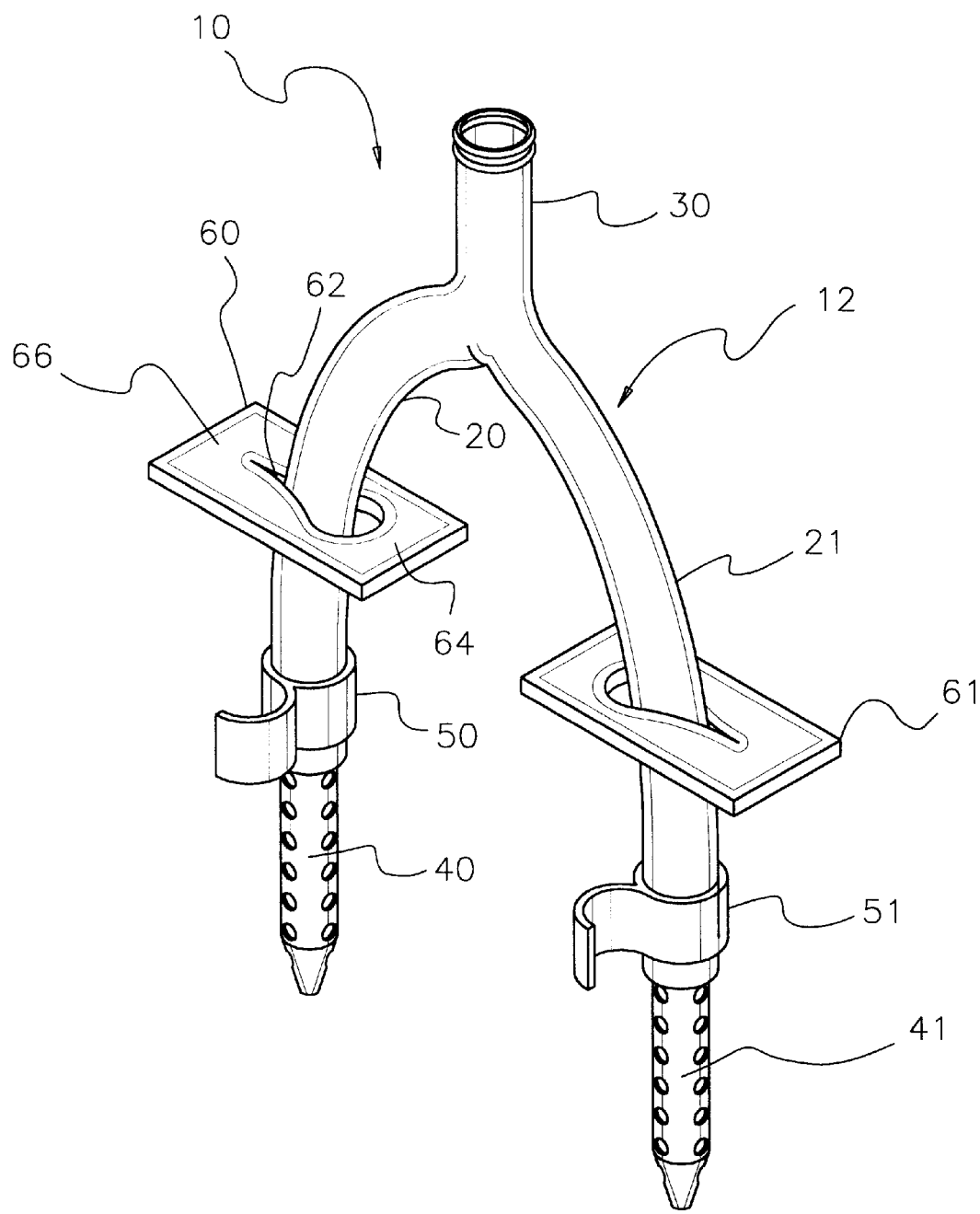
FIG. 5 is a perspective view of the present invention with the arm tube portions being pinched by the tapered end of the closing bore of the closing tabs.

Preferably, the eye and wound washing device 10 include a closure means for stopping fluid flow through the hollow interior of the Y-shaped tube member 12. Any suitable closing means may be used such as clamps or roller clamps commonly found on intravenous medical tubing. In the preferred embodiment of the invention, the closure means includes a closing tab 60,61 on each arm tube portion 20,21. As illustrated in FIGS. 2 and 3, each of the closing tabs 60,61 have closing bore 62 defined by an inner perimeter. The inner perimeter of each closing tab 60,61 is tapered from the proximal side 64 of the closing tab 60,61 towards the distal side 66 of the closing tab 60,61 so that each closing bore 62 is tapered towards its respective closing tab distal end 66. The arm tube portions 20,21 are extended through the closing bore 62 of their respective closing tab 60,61. Each arm tube portion is movable within its closing tab closing bore 62 towards and away from the tapered distal end of the closing bore 62 such that when the arm tube portion 20,21 is moved towards the tapered end of the closing bore 62 the arm tube portion 20,21 is pinched by the sides of the closing tab 60,61 inner perimeter to close fluid flow through the hollow interior of the Y-shaped tube member 12.

Ideally, the tube member 12 may be constructed of any appropriate tubing material such as plastic or a Teflon coated type of tubing. The irrigation members 40,41 may be constructed of any suitable pliable material such as plastic, latex, or rubber and can be formed in a variety of lengths and diameters to fit various sizes of wounds In use, the distal end opening 36 of the stem tube portion 30 is first connected to a fluid reservoir. The arm tube portions are positioned within their respective closing tab closing bore 62 away from the tapered end of the closing bore 62 so that fluid may flow through the tube member 12 and out the irrigation apertures 42 of irrigation members 40,41. The irrigation members may be positioned towards an eye or a wound by a user by the finger guide portions 54.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A washing device for delivering fluid to flush an eye or a wound, said eye and washing device comprising:

a hollow tube member having a first elongate arm tube portion and an elongate stem tube portion;

said stem tube portion having a proximal end, a distal end, said stem tube portion distal end having an opening into the hollow interior of said tube member, said stem tube portion distal end being connectable to a fluid reservoir to permit fluid flow from the fluid reservoir through said stem tube portion distal end opening into the hollow interior of said tube member;

said first arm tube portion being extended from said stem tube portion proximal end, said arm tube portion having a terminal end, said arm tube portion terminal end having an opening into the hollow interior of said tube member;

a first irrigator member, said first irrigator member having a hollow interior, a terminus end, an attachment end, and a plurality of irrigation apertures, said attachment end having an opening into said irrigator member hollow interior, each said irrigation aperture providing an opening through said irrigation member into said irrigation member hollow interior to permit fluid flow therethrough;

said first irrigation member attachment end opening being in fluid communication with said first arm tube portion terminal end opening;

a first guide member, said first guide member having a mounting portion and an arcuate finger guide portion, said finger guide portion being extended from said mounting portion; and said first guide member mounting portion being mounted to said first arm tube portion.

2. The washing device of claim 1, further comprising a second irrigator member, wherein said tube member has a second elongate arm tube portion, wherein said second arm tube portion is extended from said stem tube portion proximal end, said arm second tube portions having a terminal end, said arm tube portion terminal end having an opening into the hollow interior of said tube member, wherein said second irrigator member has a hollow interior, a terminus end, an attachment end, and a plurality of irrigation apertures, said attachment end having an opening into said irrigator member hollow interior, each said irrigation aperture providing an opening through said irrigation member into said irrigation member hollow interior to permit fluid flow therethrough, and wherein said second irrigation member attachment end opening is in fluid communication with said second arm tube portion terminal end opening.

3. The washing device of claim 1, wherein said terminus end of said first irrigator member is tapered for aiding insertion of said first irrigator member into a wound.

4. The washing device of claim 1, wherein said first irrigation member attachment end is inserted into said first arm tube portion terminal end opening.

5. The washing device of claim 1, wherein said first irrigation member is coupled to said first arm tube portion.

6. The washing device of claim 1, wherein said first guide member mounting portion has a mounting bore being extended therethrough, said first arm tube portion being extended through said mounting bore of said first guide member mounting portion.

7. The washing device of claim 1, wherein said finger guide portion has an outer side and an inner side, said inner side forming a concavity for receiving a finger therein, said finger guide portion being extended from said mounting portion.

8. The washing device of claim 1, further comprising a closure means for stopping fluid flow through the hollow interior of said tube member.

9. The washing device of claim 8, wherein said closure means includes a first closing tab having proximal and distal sides and an inner perimeter defining a closing bore, said closing tab inner perimeter being tapered towards said closing tab distal side such that said closing tab closing bore is tapered towards said closing tab distal end, and wherein said first arm tube portion is extended through said closing bore of said first closing tab, wherein said first arm tube is movable within said first closing tab closing bore towards and away from the tapered terminus end of said first closing tab closing bore such that said first arm tube portion is pinched by the sides of said first closing tab inner perimeter to close fluid flow through the hollow interior of said Y-shaped tube member.

10. A washing device for delivering fluid to flush an eye or a wound, said eye and washing device comprising:

- a hollow Y-shaped tube member having first and second elongate arm tube portions and an elongate stem tube portion;
- said stem tube portion having a proximal end, a distal end, said stem tube portion distal end having an opening into the hollow interior of said Y-shaped tube member, said stem tube portion distal end being couplable to a fluid reservoir to permit fluid flow from the fluid reservoir through said stem tube portion distal end opening into the hollow interior of said Y-shaped tube member;
- said first and second arm tube portions being extended from said stem tube portion proximal end, each said arm tube portions having a terminal end, said arm tube portion terminal end having an opening into the hollow interior of said Y-shaped tube member;
- first and second irrigator members, each said irrigator member having a hollow interior, a tapered terminus end, an attachment end, and a plurality of irrigation apertures, said attachment end having an opening into said irrigator member hollow interior, each said irrigation aperture providing an opening through said irrigation member into said irrigation member hollow interior to permit fluid flow therethrough;
- said first irrigation member attachment end being inserted into said first arm tube portion terminal end opening, said first irrigation member attachment end opening being in fluid communication with said first arm tube portion terminal end opening;
- said second irrigation member attachment end being inserted into said second arm tube portion terminal end opening, said second irrigation member attachment end opening being in fluid communication with said second arm tube portion terminal end opening;
- first and second guide members, each said guide member having a mounting portion and an arcuate finger guide portion, said mounting portion having a mounting bore being extended therethrough, said finger guide portion having an outer side and an inner side, said inner side forming a concavity for receiving a finger therein, said finger guide portion being extended from said mounting portion;
- said first arm tube portion being extended through said mounting bore of said first guide member mounting portion, said first guide member mounting portion being mounted to said first arm tube portion;
- said second arm tube portion being extended through said mounting bore of said second guide member mounting portion, said second guide member mounting portion being mounted to said second arm tube portion, said outer sides of said first and second guide member finger guide portions facing each other;
- first and second closing tabs, each said closing tab having proximal and distal sides and an inner perimeter defining a closing bore, said closing tab inner perimeter being tapered towards said closing tab distal side such that said closing tab closing bore is tapered towards said closing tab distal end;
- said first arm tube portion being extended through said closing bore of said first closing tab, said first arm tube being movable within said first closing tab closing bore towards the tapered terminus end of said first closing tab closing bore such that said first arm tube portion is pinched by the sides of said first closing tab inner perimeter to close fluid flow through the hollow interior of said Y-shaped tube member; and
- said second arm tube portion being extended through said closing bore of said second closing tab, said second arm tube being movable within said second closing tab closing bore towards the tapered terminus end of said second closing tab closing bore such that said second arm tube portion is pinched by the sides of said second closing tab inner perimeter to close fluid flow through the hollow interior of said Y-shaped tube member, said proximal end of said first closing tab facing said proximal end of said second closing tab.

* * * * *